(12) United States Patent
Lee et al.

(10) Patent No.: US 10,239,855 B2
(45) Date of Patent: Mar. 26, 2019

(54) PROCESS FOR PREPARING OROXYLIN A

(71) Applicant: Chia Nan University of Pharmacy and Science, Tainan (TW)

(72) Inventors: Kuan-Han Lee, Pingtung (TW); Wen-Yeuh Ho, Tainan (TW); Clay Chia-Chun Wang, Taipei (TW)

(73) Assignee: CHIA NAN UNIVERSITY OF PHARMACY AND SCIENCE, Tainan (TW)

( * ) Notice: Subject to any disclaimer, the term of this patent is extended or adjusted under 35 U.S.C. 154(b) by 76 days.

(21) Appl. No.: 15/686,380

(22) Filed: Aug. 25, 2017

(65) Prior Publication Data

US 2019/0062296 A1 Feb. 28, 2019

(51) Int. Cl.
*C07D 311/30* (2006.01)
(52) U.S. Cl.
CPC .................................. *C07D 311/30* (2013.01)
(58) Field of Classification Search
None
See application file for complete search history.

*Primary Examiner* — Heidi Reese
(74) *Attorney, Agent, or Firm* — Husch Blackwell LLP

(57) ABSTRACT

A process for preparing oroxylin A includes: subjecting baicalin to a methylation reaction using a methylating reagent in the presence of a base to methylate the 6-hydroxyl group of baicalin, so as to form a methylated compound; and subjecting the methylated compound to a deglucuronidation reaction in the presence of an acid, so as to form oroxylin A.

10 Claims, 3 Drawing Sheets

PROCESS FOR PREPARING OROXYLIN A

FIELD

The disclosure relates to a process for preparing oroxylin A, and more particularly to a process for preparing oroxylin A using baicalin as a starting material.

BACKGROUND

Oroxylin A, which is mainly found in *Scutellaria baicalensis* $G_{EORGI}$ and *Oroxylum indicum* and characterized by specific functional groups arrangement at $C_5$, $C_6$ and $C_7$, is a flavonoid having the following formula (I), in which the functional group at either one of $C_5$ and $C_7$ is a hydroxyl group, and that at $C_6$ is a methoxyl group. Much attention has been paid to the pharmacological importance of oroxylin A due to its wide physiological activities (such as pressure reduction, anti-tumor action, neuro-protection, anti-inflammation, etc.).

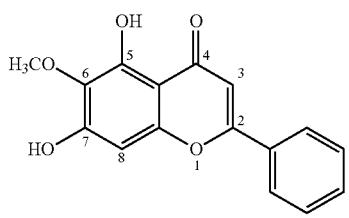

(I)

In general, oroxylin A can be extracted from plants, e.g., *Scutellaria baicalensis*, *Oroxylum indicum*, *Capparis spinosa*, *Ardisia crispa*, *Eucommia ulmoie* $O_{LIV}$, etc. However, the extraction process applied is time-consuming, cost-ineffective and unproductive. Therefore, various methods for synthesizing oroxylin A have been developed and published in articles.

In a previous study, W. H. Huang et al. reported a method for the synthesis of flavonoids (including oroxylin A) of *Scutellaria baicalensis* $G_{EORGI}$, which employs trimethoxyphenol as the starting material (Huang, W. H. et al. (2003), *Chem. Pharm. Bull.*, 51:339-340). However, the result regarding the synthesis of oroxylin A was proven to be wrong in a later study (Panhekar, D. et al. (2015), *Pharm. Res.*, 7:174-180). In fact, the actual compound synthesized in W. H. Huang et al. (2003), supra should be negletein of the following formula (II) rather than oroxylin A. This finding indicates that it is quite a challenge to correctly prepare oroxylin A using a chemical synthesis method.

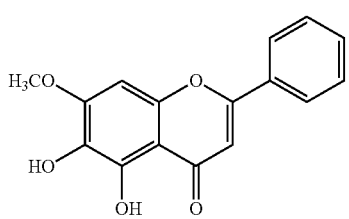

(II)

In addition, Kostrzewa-Susłow et al. reported microbial transformation of baicalein (5,6,7-trihydroxyflavone) and baicalin (baicalein-7-O-glucuronide) into oroxylin A after six days of incubation with *Chaetomium* sp. (Kostrzewa-Susłowa, E. et al. (2007), *J. of Mol. Catal. B: Enzym.*, 49:113-117).

Chen disclosed use of 2,4,6-trinitrotoluene as a starting material for synthesizing oroxylin A (Chen, C. P. (2008), *Yearbook of Chinese Medicine and Pharmacy*, 26:241-358).

CN 101508689 B disclosed a method for synthesizing oroxylin A using baicalein as the starting material. The method includes the steps of: (a) adding a protecting group to $C_7$ position of baicalein; (b) methylating the hydroxyl group at $C_6$ position; and (c) removing the protecting group at $C_7$ position to obtain oroxylin A.

It is noted that the aforesaid chemical synthesis methods are complicated and the reaction conditions required are stringent, and the above-mentioned microbial transformation is time-consuming.

SUMMARY

Therefore, an object of the disclosure is to provide a process for preparing oroxylin A that can alleviate at least one of the drawbacks of the prior art.

The preparation process of the disclosure includes:
subjecting baicalin to a methylation reaction using a methylating reagent in the presence of a base to methylate the 6-hydroxyl group of baicalin, so as to form a methylated compound; and
subjecting the methylated compound to a deglucuronidation reaction in the presence of an acid, so as to form oroxylin A.

BRIEF DESCRIPTION OF THE DRAWINGS

Other features and advantages of the disclosure will become apparent in the following detailed description of the embodiment with reference to the accompanying drawings, of which.

DETAILED DESCRIPTION

Figure 1:
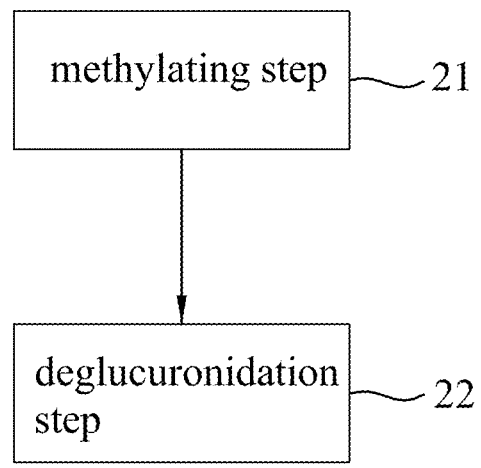
FIG. 1 is a flow chart illustrating an embodiment of a process for preparing oroxylin A.

Referring to FIG. 1, an embodiment of a process for preparing oroxylin A according to the disclosure includes a methylating step 21 and a deglucuronidation step 22.

According to the disclosure, in the methylating step 21, baicalin (serving as a starting material) is subjected to a methylation reaction using a methylating reagent in the presence of a base to methylate the 6-hydroxyl group of baicalin, so as to form a methylated compound.

Examples of the base suitable for use in the preparation process of this disclosure include, but are not limited to, potassium carbonate, sodium carbonate, cesium carbonate, potassium bicarbonate, sodium bicarbonate and combinations thereof.

Examples of the methylating reagent suitable for use in the preparation process of this disclosure include, but are not limited to, dimethyl sulfate (DMS), iodomethane and a combination thereof.

In certain embodiments, the mole ratio of the methylating reagent to baicalin may be not less than 5.

In certain embodiments, the methylation reaction may be conducted at a temperature ranging from an ambient temperature to 80° C. In an exemplary embodiment, the methylation reaction is conducted at an ambient temperature.

It has been known that the γ-pyrone ring of flavonoids (such as oroxylin A) readily decomposes under basic conditions. Therefore, processes for the preparation of flavonoids or any reaction involving flavonoids normally has to be conducted under more stringent conditions (e.g. in the presence of dehydrated chemical reagents or an inert gas), otherwise the hydrolysis of γ-pyrone ring would cause formation of undesired products and a low yield of a target compound. In endeavoring to efficiently prepare oroxylin A, the applicants found that: the hydroxyl groups on the glucuronate of baicalin will not interfere with the methylation reaction of the 6-hydroxyl group of baicalin, which means that a glucuronate can be substantially deemed a protection group for the 7-hydroxyl group of baicalein. It was also found that by using baicalin as a starting material and by applying a methylating reagent instead of an organic solvent to conduct the methylation reaction under a basic condition, the hydrolysis of γ-pyrone ring can be effectively prevented, thereby avoiding generation of undesired products and simplifying any necessary purification process. In addition, the reaction conditions required can also be simplified, since the methylation reaction can be performed in an atmospheric environment instead of an inert gas environment and the methylating reagent does not need to be dehydrated.

According to the disclosure, in the deglucuronidation step 22, the methylated compound is subjected to a deglucuronidation reaction in the presence of an acid, so as to form oroxylin A. In other words, the glucuronate of the methylated compound can be removed under an acidic condition.

Examples of the acid suitable for use in the preparation process of this disclosure include, but are not limited to, hydrochloric acid, sulfuric acid, nitric acid, and combinations thereof.

In certain embodiments, the deglucuronidation reaction may be carried out in the presence of a polar solvent. Examples of the polar solvent suitable for use in the preparation process of this disclosure include, but are not limited to, methanol, ethanol, 1-propanol, isopropanol, and combinations thereof.

In certain embodiments, the deglucuronidation reaction may be conducted at a temperature ranging from an ambient temperature to 120° C., preferably from 40° C. to 100° C., and more preferably from 40° C. to 80° C.

It should be noted that like the methylation reaction, all other reaction steps in the preparation process of the disclosure may be performed in an atmospheric environment without supplying any inert gas.

In certain embodiments, the preparation process of the disclosure may further include purifying the methylated compound prior to the deglucuronidation step 22, and the purified methylated compound is used to conduct the deglucuronidation step 22.

In certain embodiments, the methylating step 21 and the deglucuronidation step 22 may be conducted in one pot.

As used herein, the term "one pot reaction" or equivalents thereof, e.g., "1-pot", "one pot", etc., mean that when a target compound is synthesized through a reaction procedure comprising two or more steps, products of individual steps (intermediate products) are allowed to continuously react with the reactant of the next step in a reactor without any purification thereof, thus obtaining a desired compound.

The disclosure will be further described by way of the following examples. However, it should be understood that the following examples are solely intended for the purpose of illustration and should not be construed as limiting the disclosure in practice.

EXAMPLES

Oroxylin A was prepared according to the following reaction scheme and protocol.

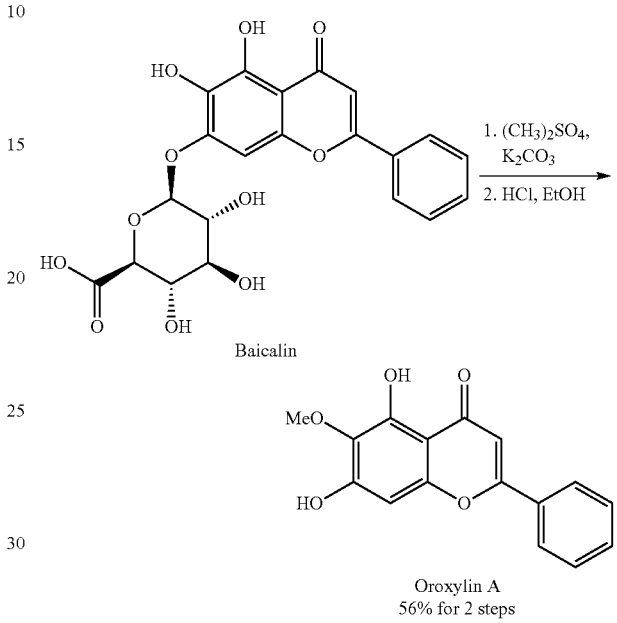

To be specific, baicalin (223 mg, 0.5 mmole) serving as a starting material was mixed with dimethyl sulfate (1.26 g, 10 mmole) and potassium carbonate (345 mg, 2.5 mmole) in a reaction bottle under agitation at room temperature, so as to methylate the 6-hydroxyl group of baicalin.

Thereafter, to the resultant mixture was added a solution of HCl/ethanol mixture (10 mL, HCl/ethanol=1:9), so that a deglucuronidation reaction was conducted at 80° C. for 10 to 12 hours, followed by cooling to room temperature. After addition of water and extraction with ethyl acetate, the resultant organic layer was collected and subjected to concentration, followed by purification via silica gel column chromatography. Thus, oroxylin A (80 mg, 56% yield) was obtained.

Figure 2:
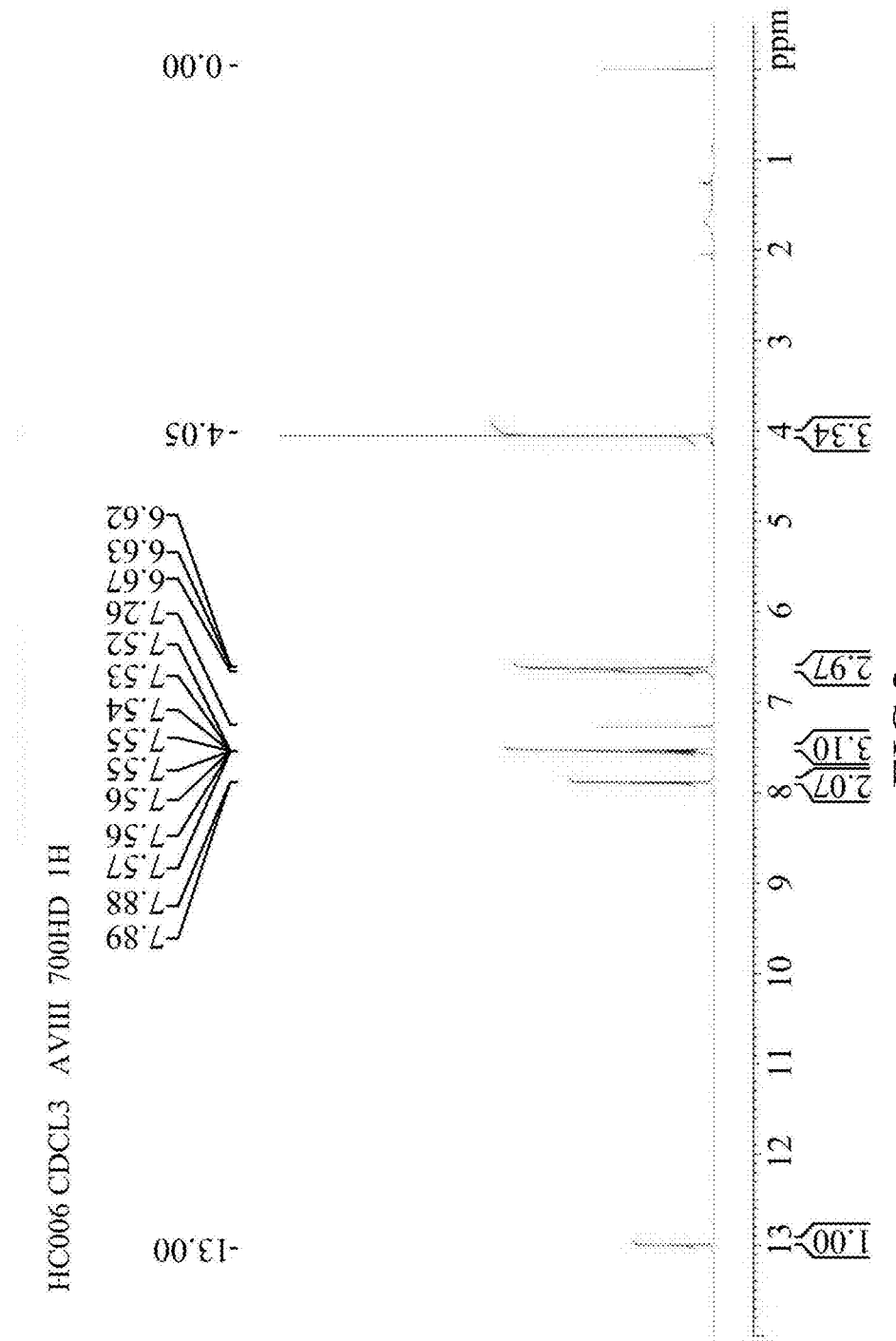
FIG. 2 is a $^1$H NMR spectrum of oroxylin A prepared by the process of the disclosure, which was recorded using CDCl$_3$ as solvent.
Figure 3:
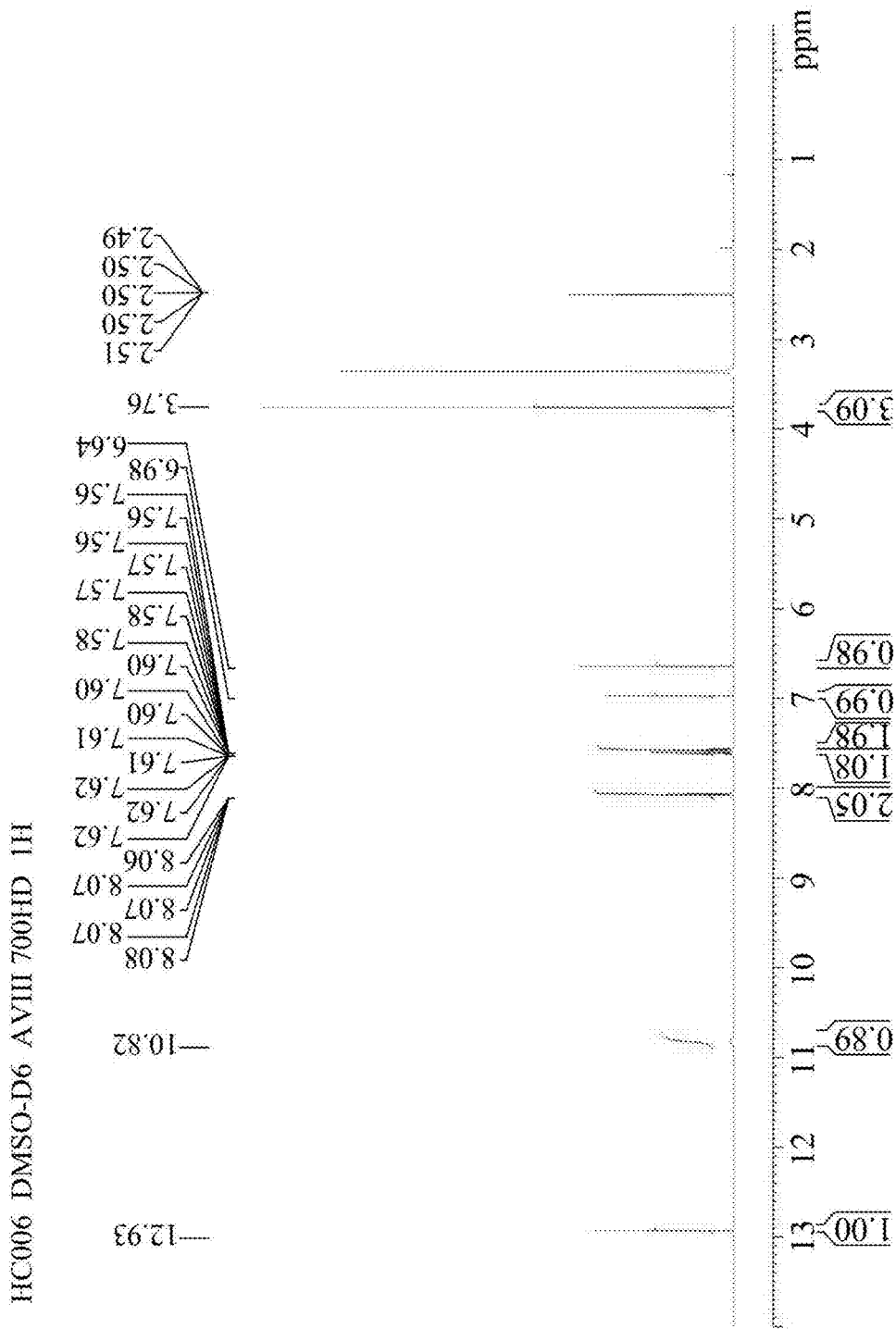
FIG. 3 is a $^1$H NMR spectrum of oroxylin A prepared by the process of the disclosure, which was recorded using DMSO-d$_6$ as solvent.

FIGS. 2 and 3 show the $^1$H-NMR spectra of oroxylin A obtained according to the preparation process of the disclosure, which were respectively recorded using CDCl$_3$ and DMSO-d$_6$ as a solvent. The detailed data detected are summarized as follows.

$^1$H NMR (700 MHz, CDCl$_3$): δ 13.00 (s, 1H), 7.89-7.88 (m, 2H), 7.56-7.52 (m, 3H), 6.67 (s, 1H), 6.63 (s, 1H), 6.62 (s, 1H), 4.05 (s, 3H).

$^1$H NMR (700 MHz, DMSO-d$_6$): δ 12.93 (s, 1H), 10.82 (s, 1H), 8.08-8.06 (m, 2H), 7.62-7.56 (m, 3H), 6.98 (s, 1H), 6.64 (s, 1H), 3.76 (s, 3H).

After comparing the above-mentioned $^1$H-NMR spectra with the spectra disclosed in Chen, C. P. (2008), supra and in Panhekar, D. et al. (2015), supra, the compound obtained in this example was confirmed to be oroxylin A. Therefore, the applicant contemplates that the process of the present disclosure can be used to correctly prepare oroxylin A.

In addition, oroxylin A can be efficiently prepared through the process of the present disclosure (namely, by selecting baicalin as a starting material), since the glucuronate at C7 position (which can serve as a protection group for the C7-hydroxyl group of baicalein) will not interfere with the methylation of the hydroxyl group at C6 position of baicalin and thereafter can be readily removed under an acidic condition in an atmospheric environment.

In the description above, for the purposes of explanation, numerous specific details have been set forth in order to provide a thorough understanding of the embodiment. It will be apparent, however, to one skilled in the art, that one or more other embodiments may be practiced without some of these specific details. It should also be appreciated that reference throughout this specification to "one embodiment," "an embodiment," and so forth means that a particular feature, structure, or characteristic may be included in the practice of the disclosure. It should be further appreciated that in the description, various features are sometimes grouped together in a single embodiment or description thereof for the purpose of streamlining the disclosure and aiding in the understanding of various inventive aspects.

While the disclosure has been described in connection with what is considered the exemplary embodiment, it is understood that this disclosure is not limited to the disclosed embodiment but is intended to cover various arrangements included within the spirit and scope of the broadest interpretation so as to encompass all such modifications and equivalent arrangements.

What is claimed is:

1. A process for preparing oroxylin A, comprising:
    subjecting baicalin to a methylation reaction using a methylating reagent in the presence of a base to methylate the 6-hydroxyl group of baicalin, so as to form a methylated compound; and
    subjecting the methylated compound to a deglucuronidation reaction in the presence of an acid, so as to form oroxylin A.

2. The process of claim 1, wherein the base is selected from the group consisting of potassium carbonate, sodium carbonate, cesium carbonate, potassium bicarbonate, sodium bicarbonate and combinations thereof.

3. The process of claim 1, wherein the methylating reagent is selected from the group consisting of dimethyl sulfate, iodomethane and a combination thereof.

4. The process of claim 1, wherein the acid is selected from the group consisting of hydrochloric acid, sulfuric acid, nitric acid, and combinations thereof.

5. The process of claim 1, wherein the deglucuronidation reaction is carried out in the presence of a polar solvent selected from methanol, ethanol, 1-propanol, isopropanol, and combinations thereof.

6. The process of claim 1, wherein the methylation reaction is conducted at a temperature ranging from an ambient temperature to 80° C.

7. The process of claim 1, wherein the deglucuronidation reaction is conducted at a temperature ranging from an ambient temperature to 120° C.

8. The process of claim 6, wherein the deglucuronidation reaction is conducted at a temperature ranging from an ambient temperature to 120° C.

9. The process of claim 1, wherein the methylation reaction is conducted at an ambient temperature, and the deglucuronidation reaction is conducted at a temperature ranging from 40° C. to 80° C.

10. The process of claim 1, wherein the methylation reaction and the deglucuronidation reaction are conducted in one pot.

* * * * *